(12) United States Patent
Nishino et al.

(10) Patent No.: US 9,272,971 B2
(45) Date of Patent: Mar. 1, 2016

(54) CATALYST FOR C2 OXYGENATE SYNTHESIS, DEVICE FOR MANUFACTURING C2 OXYGENATE, AND METHOD FOR MANUFACTURING C2 OXYGENATE

(71) Applicants: Sekisui Chemical Co., Ltd., Osaka (JP); NATIONAL INSTITUTE OF ADVANCED INDUSTRIAL SCIENCE AND TECHNOLOGY, Tokyo (JP)

(72) Inventors: Tomoaki Nishino, Ibaraki (JP); Toshihito Miyama, Ibaraki (JP); Kazuhisa Murata, Ibaraki (JP); Yanyong Liu, Ibaraki (JP)

(73) Assignees: SEKISUI CHEMICAL CO., LTD., Osaka (JP); NATIONAL INSTITUTE OF ADVANCED INDUSTRIAL SCIENCE AND TECHNOLOGY, Tokyo (JP)

( * ) Notice: Subject to any disclaimer, the term of this patent is extended or adjusted under 35 U.S.C. 154(b) by 51 days.

(21) Appl. No.: 14/240,108

(22) PCT Filed: Feb. 28, 2013

(86) PCT No.: PCT/JP2013/055532
§ 371 (c)(1),
(2) Date: Feb. 21, 2014

(87) PCT Pub. No.: WO2013/129614
PCT Pub. Date: Sep. 6, 2013

(65) Prior Publication Data
US 2014/0194541 A1      Jul. 10, 2014

(30) Foreign Application Priority Data

Feb. 28, 2012 (JP) ................. 2012-041775
Jul. 27, 2012 (JP) ................. 2012-167725
Aug. 22, 2012 (JP) ................. 2012-183389

(51) Int. Cl.
| | | |
|---|---|---|
| *B01J 23/00* | (2006.01) | |
| *B01J 23/02* | (2006.01) | |
| *C07C 29/153* | (2006.01) | |
| *C07C 29/158* | (2006.01) | |
| *C07C 45/49* | (2006.01) | |
| *C07C 51/10* | (2006.01) | |
| *B01J 37/02* | (2006.01) | |
| *B01J 21/06* | (2006.01) | |
| *B01J 23/656* | (2006.01) | |
| *B01J 35/10* | (2006.01) | |
| *B01J 8/06* | (2006.01) | |

(52) U.S. Cl.
CPC ............. *C07C 29/153* (2013.01); *B01J 8/06* (2013.01); *B01J 21/063* (2013.01); *B01J 23/6562* (2013.01); *B01J 35/1019* (2013.01); *B01J 35/1023* (2013.01); *B01J 35/1038* (2013.01); *B01J 35/1057* (2013.01); *B01J 35/1061* (2013.01); *B01J 37/0201* (2013.01); *B01J 37/024* (2013.01); *C07C 29/158* (2013.01); *C07C 45/49* (2013.01); *C07C 51/10* (2013.01); *Y02P 20/52* (2015.11)

(58) Field of Classification Search
CPC ...... B01J 35/1052; B01J 21/12; B01J 21/063; B01J 23/04; B01J 23/464; C07C 51/10
USPC ................... 502/300, 344; 518/700
See application file for complete search history.

(56) References Cited

U.S. PATENT DOCUMENTS

| | | | |
|---|---|---|---|
| 4,235,798 A | 11/1980 | Bartley et al. | |
| 7,612,013 B2 * | 11/2009 | Sato et al. | ..... 502/325 |
| 2007/0249874 A1 | 10/2007 | Luo et al. | |

FOREIGN PATENT DOCUMENTS

| | | |
|---|---|---|
| CA | 2 895 331 | 6/2014 |
| CN | 1942243 | 4/2007 |
| EP | 0 021 443 | 1/1981 |
| EP | 2 876 100 | 5/2015 |
| JP | 61-36730 | 8/1986 |
| JP | 61-36731 | 8/1986 |
| JP | 2007-526119 | 9/2007 |
| JP | 2007-314745 | 12/2007 |
| JP | 2010-188238 | 9/2010 |
| JP | 2012-1441 | 1/2012 |
| WO | 2005/084799 | 9/2005 |
| WO | 2014/097942 | 6/2014 |

OTHER PUBLICATIONS

Bao et al, precedure and catalyst for C2-oxygenates from syngas, DE 10132500 Abstract, Jan. 2003.*
International Search Report issued May 7, 2013 in International (PCT) Application No. PCT/JP2013/055532.
Office Action dated Jul. 29, 2015 in corresponding Chinese Application No. 201380002540.7, with partial English translation.
Extended European Search Report issued Sep. 21, 2015 in corresponding European Application No. 13754702.2.

* cited by examiner

*Primary Examiner* — Jafar Parsa
(74) *Attorney, Agent, or Firm* — Wenderoth, Lind & Ponack, L.L.P.

(57) ABSTRACT

The present invention relates to a catalyst for C2 oxygenate synthesis in which a hydrogenated active metal is supported on a porous carrier to synthesize a C2 oxygenate from a mixed gas containing hydrogen and carbon monoxide, wherein the porous carrier has an average pore diameter of 0.1 to 20 nm.

5 Claims, 2 Drawing Sheets

CATALYST FOR C2 OXYGENATE SYNTHESIS, DEVICE FOR MANUFACTURING C2 OXYGENATE, AND METHOD FOR MANUFACTURING C2 OXYGENATE

TECHNICAL FIELD

The present invention relates to a catalyst for C2 oxygenate synthesis, a device for manufacturing a C2 oxygenate, and a method for manufacturing a C2 oxygenate.

Priority is claimed on Japanese Patent Application No. 2012-041775, filed Feb. 28, 2012, Japanese Patent Application No. 2012-167725, filed Jul. 27, 2012, and Japanese Patent Application No. 2012-183389 filed Aug. 22, 2012, the contents of which are incorporated herein by reference.

BACKGROUND ART

Bioethanol is becoming more widespread as an alternative fuel to petroleum. Bioethanol is mainly manufactured by the saccharification and fermentation of sugar cane or maize. In recent years, techniques have been developed for manufacturing bioethanol from wood-based or plant-based biomass (also known as cellulose-based biomass), including the unused portions of crops such as waste wood or rice straw, which are not in competition for use as foodstuffs or animal feed.

In order to use a cellulose-based biomass as a raw material, and enable the manufacture of bioethanol using a conventional ethanol fermentation method, the cellulose must be saccharified. Examples of the saccharification method include a concentrated sulfuric acid saccharification method, a dilute sulfuric acid-enzymatic saccharification method, and a heated water saccharification method, but many problems still remain to manufacturing bioethanol inexpensively.

On the other hand, another method exists in which the cellulose-based biomass is converted to a mixed gas containing hydrogen and carbon monoxide, and ethanol is then synthesized from this mixed gas. With this method, tests are being conducted with the aim of manufacturing bioethanol efficiently from cellulose-based biomass that is difficult to use in the ethanol fermentation method. This method is not limited to wood-based and plant-based biomass, but can use all manner of organic matter as the raw material, such as animal-based biomass derived from animal corpses and feces; biomass derived from raw garbage, waste paper and waste fiber; and plastic.

Moreover, the mixed gas of hydrogen and carbon monoxide can also be obtained from resources besides petroleum, including natural gas and coal, and therefore methods of synthesizing C2 oxygenates, such as ethanol, acetaldehyde and acetic acid, from this type of mixed gas are also being researched as potential techniques for breaking away from petroleum dependency.

Examples of known methods for obtaining C2 oxygenates from a mixed gas of hydrogen and carbon monoxide include methods in which, for example, the mixed gas is brought into contact with a catalyst in which rhodium and an alkali metal are supported on a silica gel carrier (for example, see Patent Documents 1 and 2).

DOCUMENTS OF RELATED ART

Patent Documents

Patent Document 1: Japanese Examined Patent Application, Second Publication No. Sho 61-36730

Patent Document 2: Japanese Examined Patent Application, Second Publication No. Sho 61-36731

SUMMARY OF THE INVENTION

Problems to be Solved by the Invention

The ability of a catalyst for C2 oxygenate synthesis is evaluated by indicators such as a CO conversion rate, selectivity, and a space time yield of a C2 oxygenate.

The term "CO conversion rate" means the percentage indicating the number of moles of CO consumed among the total number of moles of CO within the mixed gas.

The "selectivity" is a percentage indicating the number of moles of C converted to a specific oxygenate among the number of moles of CO consumed from the mixed gas. For example, in the formula (α) shown below, the selectivity for ethanol, which represents one C2 oxygenate, is 100 mol %. On the other hand, in the formula (β) shown below, the selectivity for ethanol, which represents one C2 oxygenate, is 50 mol %, and the selectivity for acetaldehyde, which represents another C2 oxygenate, is also 50 mol %. In the formulae (α) and (β), the selectivity for a C2 oxygenate is 100 mol %.

$$4H_2 + 2CO \rightarrow CH_3CH_2OH + H_2O \quad (\alpha)$$

$$7H_2 + 4CO \rightarrow C_2H_5OH + CH_3CHO + 2H_2O \quad (\beta)$$

The "space time yield of a C2 oxygenate" is an amount of a synthesized C2 oxygenate per unit volume of the catalyst, per unit time (g/L-catalyst/h), and is proportional to the product of a CO conversion rate and selectivity for a C2 oxygenate. Therefore, if a catalyst significantly lowers either the CO conversion rate or the selectivity for a C2 oxygenate, the space time yield of a C2 oxygenate cannot be increased.

In conventional methods for manufacturing C2 oxygenates which utilize catalysts for C2 oxygenate syntheses, although selectivity for C2 oxygenates can be increased, CO conversion rates cannot sufficiently be increased, and consequently space time yields of C2 oxygenates are not sufficiently be increased.

To solve this problem, the present invention aims to provide a catalyst for C2 oxygenate synthesis which produces a C2 oxygenate having a higher proportion of ethanol, resulting in efficient synthesis of ethanol; and a catalyst for C2 oxygenate synthesis which is capable of increasing a space time yield of a C2 oxygenate.

Means to Solve the Problems

The present invention relates to the following aspects.

[1] A catalyst for C2 oxygenate synthesis in which a hydrogenated active metal is supported on a porous carrier to synthesize a C2 oxygenate from a mixed gas containing hydrogen and carbon monoxide, wherein the porous carrier has an average pore diameter of 0.1 to 20 nm.

[2] The catalyst for C2 oxygenate synthesis according to [1], wherein the average pore diameter is 0.1 to 8 nm.

[2] The catalyst for C2 oxygenate synthesis according to [1], wherein a mode of pore diameters of the porous carrier is 0.1 to 8 nm.

[4] The catalyst for C2 oxygenate synthesis according to [1], wherein the average pore diameter is 2 to 20 nm.

[5] The catalyst for C2 oxygenate synthesis according to [1], wherein a mode of pore diameters of the porous carrier is 2 to 20 nm.

[6] The catalyst for C2 oxygenate synthesis according to [2] or [3], wherein the hydrogenated active metal is one or more substances selected from the group consisting of alkali metals and elements belonging to groups 7 to 10 of the periodic table.

[7] The catalyst for C2 oxygenate synthesis according to [4] or [5], wherein the hydrogenated active metal is one or more substances selected from the group consisting of alkali metals and elements belonging to groups 7 to 10 of the periodic table.

[8] The catalyst for C2 oxygenate synthesis according to any one of [1] to [7], wherein the C2 oxygenate is at least one selected from the group consisting of ethanol, acetaldehyde and acetic acid.

[9] The catalyst for C2 oxygenate synthesis according to any one of [1] to [8], wherein the catalyst for C2 oxygenate synthesis contains rhodium, manganese and lithium.

[10] The catalyst for C2 oxygenate synthesis according to any one of [1] to [9], wherein the catalyst for C2 oxygenate synthesis further contains titanium or magnesium.

[11] The catalyst for C2 oxygenate synthesis according to any one of [1] to [10], wherein a specific surface area of the porous carrier is 400 to 700 m$^2$/g.

[12] The catalyst for C2 oxygenate synthesis according to any one of [1] to [11], wherein a value represented by (total pore volume)/(specific surface area×average pore diameter) of the porous carrier is 0.2 to 0.5.

[13] The catalyst for C2 oxygenate synthesis according to any one of [1] to [12], wherein the hydrogenated active metal is an alkali metal, and a supported amount of the hydrogenated active metal is 0.125 to 10 parts by mass provided that the amount of the porous carrier is 100 parts by mass.

[14] The catalyst for C2 oxygenate synthesis according to any one of [1] to [13], wherein the hydrogenated active metal is an element belonging to group 7 of the periodic table, and a supported amount of the hydrogenated active metal is 0.25 to 10 parts by mass provided that the amount of the porous carrier is 100 parts by mass.

[15] The catalyst for C2 oxygenate synthesis according to any one of [1] to [14], wherein a supported amount of the auxiliary active metal is 1 to 10 parts by mass provided that the amount of the porous carrier is 100 parts by mass.

[16] A device for manufacturing a C2 oxygenate, the device including a reaction tube packed with the catalyst for C2 oxygenate synthesis according to any one of [1] to [15], a supply unit for supplying the mixed gas into the reaction tube, and a discharge unit for discharging the product from the reaction tube.

[17] A method for manufacturing a C2 oxygenate, wherein the C2 oxygenate is obtained by bringing a mixed gas containing hydrogen and carbon monoxide into contact with the catalyst for C2 oxygenate synthesis according to any one of [1] to [15].

[18] The method for manufacturing a C2 oxygenate according to [17], wherein a space time yield of the C2 oxygenate is 650 (g/L-catalyst/h) to 180 (g/L-catalyst/h).

[19] The method for manufacturing a C2 oxygenate according to [17], wherein selectivity for ethanol in the C2 oxygenate is 96 mol % to 35 mol %.

In the present description, the C2 oxygenate describes a molecule composed of carbon, hydrogen and oxygen atoms, which has two carbon atoms, and examples include acetic acid, ethanol and acetaldehyde.

Effects of the Invention

By utilizing the catalyst for C2 oxygenate synthesis according to the present invention, the C2 oxygenate having a higher proportion of ethanol can be produced and/or a space time yield of the C2 oxygenate can be increased to efficiently synthesize the C2 oxygenate, in particular ethanol.

EMBODIMENTS FOR CARRYING OUT THE INVENTION (Catalyst for C2 Oxygenate Synthesis)

A catalyst for C2 oxygenate synthesis according to the present invention (hereafter also referred to as simply "the catalyst") synthesizes the C2 oxygenate from a mixed gas containing hydrogen and carbon monoxide, and the catalyst is a so-called "supported catalyst" in which a hydrogenated active metal is supported on a porous carrier.

A material of the porous carrier is not particularly limited, and examples include silica, zirconia, titania and magnesia. Of these, silica is preferable because various products having differing specific surface areas and pore diameters can be procured commercially.

A size of the porous carrier is not particularly limited, and for example, when the porous carrier is made from silica, the pore size is preferably 0.5 to 5000 μm. The pore size of the porous carrier is adjusted by screening.

In addition, the porous carrier is preferably a substance having a particle size distribution as narrow as possible.

The sum of pore volumes (total pore volume) in the porous carrier is not particularly limited, and for example, the total pore volume is preferably 0.01 to 1.0 mL/g, more preferably 0.1 to 0.8 mL/g, and still more preferably 0.3 to 0.7 mL/g. If the total pore volume is less than the aforementioned lower limit, a sufficient specific surface area of the porous carrier cannot be obtained, and thus supported amounts of a hydrogenated active metal and an auxiliary active metal (the auxiliary active metal will be explained later) (hereafter, these are collectively referred to as "catalyst metal") become insufficient. As a result, there is a possibility that the CO conversion rate is decreased. If the total pore volume exceeds the aforementioned upper limit, a diffusion rate of the raw material mixed gas becomes too fast to keep sufficient contact between the catalyst and the mixed gas, and thus there is a possibility that selectivity for ethanol is decreased.

The total pore volume is a value measured by the aqueous titration method. In the aqueous titration method, water molecules are adsorbed onto a surface of the porous carrier, and pore distribution is measured by condensation of the molecules.

The term "CO conversion rate" means the percentage indicating the number of moles of CO consumed among the total number of moles of CO within the mixed gas.

The "selectivity" is a percentage indicating the number of moles of C converted to a specific C2 oxygenate among the number of moles of CO consumed from the mixed gas. For example, in the formula (a) shown below, the selectivity for ethanol, which represents the C2 oxygenate, is 100 mol %. On the other hand, in the formula (β) shown below, the selectivity for ethanol, which represents one C2 oxygenate, is 50 mol %, and the selectivity for acetaldehyde, which represents another C2 oxygenate, is also 50 mol %.

Although the average pore diameter of the porous carrier is preferably 0.1 to 20 nm, from the viewpoint of selectivity for the C2 oxygenate, preferably selectivity for ethanol, the average pore diameter is preferably 0.1 to 8 nm, more preferably 0.1 to 5 nm, and still more preferably 1 to 4 nm. If the average pore diameter is less than the aforementioned lower limit, a supported amount of the catalyst metal is decreased, and thus the CO conversion rate is also decreased. If the average pore diameter exceeds the aforementioned upper limit, a diffusion rate of the mixed gas becomes too fast to keep sufficient contacting time between the catalyst metal and the mixed gas, and thus selectivity for the C2 oxygenate, in particular selectivity for ethanol is decreased. In addition, if the average pore diameter is not greater than the aforementioned upper limit, a specific surface area of the porous carrier becomes sufficiently large to increase efficiency of heat transfer to the catalyst, and thereby the C2 oxygenate can be synthesized more efficiently. Thus, if the average pore diameter is not greater than the aforementioned upper limit, the C2 oxygenate, in particular ethanol can be synthesized more efficiently.

From the viewpoint of the space time yield of the C2 oxygenate, the average pore diameter of the porous carrier is preferably 2 to 20 nm; more preferably greater than 5 nm, but less than 14 nm; and still more preferably greater than 5 nm, but not greater than 10 nm. If the average pore diameter is less than the aforementioned lower limit, a supported amount of the catalyst metal is decreased, and thus the CO conversion rate is also decreased. If the average pore diameter exceeds the aforementioned upper limit, a diffusion rate of the mixed gas becomes too fast to keep sufficient contacting time between the catalyst metal and the mixed gas, and thus selectivity for the C2 oxygenate, preferably selectivity for ethanol is decreased. That is, if the average pore diameter is within the aforementioned range, suitable contacting time between the catalyst metal and the mixed gas is obtained to increase the space time yield of the C2 oxygenate, and thereby the C2 oxygenate can be synthesized more efficiently.

In the present description, the term "space time yield of the C2 oxygenate" means a value obtained when all C2 oxygenates are assumed to be converted into ethanol by a well-known hydrogen reduction treatment (for example, catalytic hydrogen reduction).

If the average pore diameter is not greater than the aforementioned upper limit, a specific surface area of the porous carrier becomes sufficiently large to increase efficiency of heat transfer to the catalyst, and thereby the C2 oxygenate can be synthesized more efficiently. The average pore diameter is a value measured by the technique described below. When the average pore diameter is at least as large as 0.1 nm, but is less than 10 nm, the average pore diameter is calculated from the total pore volume and the BET specific surface area. When the average pore diameter is at least as large as 10 nm, the average pore diameter is measured by the mercury penetration method using a porosimeter.

Here, the total pore volume is a value measured by the aqueous titration method, and the BET specific surface area is a value calculated from an adsorbed amount of nitrogen that is an adsorption gas, and a pressure at the time of adsorption.

In the mercury penetration method, a pressure is applied to penetrate mercury into pores of the porous carrier, and the average pore diameter is calculated from the pressure and an amount of the penetrated mercury.

From the viewpoint of selectivity for the C2 oxygenate, preferably selectivity for ethanol, a mode of pore diameters of the porous carrier is preferably 0.1 to 8 nm, more preferably 0.1 to 5 nm, and still more preferably 1 to 4 nm. From the viewpoint of the space time yield of the C2 oxygenate, preferably of ethanol, a mode of pore diameters of the porous carrier is preferably 2 to 20 nm; more preferably greater than 5 nm, but less than 14 nm; and still more preferably greater than 5 nm, but not greater than 10 nm.

Although the specific surface area of the porous carrier is not particularly limited, for example, it is preferably 1 to 1000 m$^2$/g, more preferably 450 to 1000 m$^2$/g, still more preferably 300 to 800 m$^2$/g, particularly preferably 400 to 700 m$^2$/g, and more particularly preferably 500 to 700 m$^2$/g. If the specific surface area is at least as large as the aforementioned lower limit, a supported amount of the catalyst metal becomes sufficient to further increase the CO conversion rate. In addition, if the specific surface area is at least as large as the aforementioned lower limit, the C2 oxygenate can be synthesized more efficiently. The reason of the above is thought to be the following: by using the porous carrier having a large specific surface area, efficiency of heat transfer to the catalyst is increased, and thereby the synthetic reaction of the C2 oxygenate is more facilitated.

If the specific surface area is not greater than the aforementioned upper limit, a more suitable diffusion rate of the mixed gas is obtained to further increase selectivity for ethanol.

The specific surface area means the BET specific surface area, which is measured by the BET gas adsorption method using nitrogen as an adsorption gas.

In the porous carrier, the product of the total pore volume and the specific surface area is preferably 1 to 1000 mL·m$^2$/g$^2$, and more preferably 100 to 500 mL·m$^2$/g$^2$. If the product is at least as large as the aforementioned lower limit, a supported amount of catalyst metal becomes sufficient to further increase the CO conversion rate.

If the product is not greater than the aforementioned upper limit, a more suitable diffusion rate of the mixed gas is obtained to further increase selectivity for the C2 oxygenate, preferably selectivity for ethanol. That is, if the product is within the aforementioned range, a space time yield of the C2 oxygenate can further be increased.

In the porous carrier, the value represented by (total pore volume)/(specific surface area×average pore diameter)(hereafter also referred to as the ratio of volume/area·diameter) is preferably 0.1 to 1, and more preferably 0.2 to 0.5. If the ratio is at least as large as the aforementioned lower limit, porosity of the porous carrier becomes sufficient to further increase the CO conversion rate, and if the ratio is not greater than the aforementioned upper limit, a more suitable diffusion rate of the mixed gas is obtained to further increase selectivity for the C2 oxygenate. That is, if the ratio of volume/area·diameter is within the aforementioned range, a space time yield of the C2 oxygenate can further be increased.

For example, the ratio of volume/area·diameter of the porous carrier having the total pore volume of 0.61 mL/g, the specific surface area of 430 m$^2$/g, and the average pore diameter of 5.7 nm can be determined by the formula (i) shown below.

$$\text{Ratio of Volume/Area·Diameter} = (0.61 \times 10^{-6} \text{m}^3/\text{g}) / \{(430 \text{ m}^2/\text{g}) \times (5.7 \times 10^{-9} \text{ m})\} 0.249 \quad \text{(i)}$$

As the hydrogenated active metal, a well-known metal capable of synthesizing the C2 oxygenate from the mixed gas can be used, and examples include alkali metals such as lithium and sodium; elements belonging to group 7 of the periodic table, such as manganese and rhenium; elements belonging to group 8 of the periodic table, such as ruthenium; elements belonging to group 9 of the periodic table, such as cobalt and rhodium; and elements belonging to group 10 of the periodic table, such as nickel and palladium.

These hydrogenated active metals may be used as one type, or may be used as two or more types in combination. For example, from the viewpoint of further increasing the CO conversion rate and selectivity for ethanol, the hydrogenated active metal is preferably a combination of rhodium, an alkali metal, and another hydrogenated active metal; or a combination of ruthenium, an alkali metal, and another hydrogenated active metal, and examples include a combination of rhodium, manganese and lithium; and a combination of ruthenium, rhenium and sodium.

In the catalyst, a supported amount of the hydrogenated active metal is determined with due consideration of the type of the hydrogenated active metal, the material of the porous carrier and the like.

When an alkali metal is used as the hydrogenated active metal, a supported amount of the hydrogenated active metal is preferably 0.001 to 30 parts by mass, and more preferably 0.125 to 10 parts by mass provided that the amount of the porous carrier is 100 parts by mass. If the supported amount is less than the aforementioned lower limit, the supported amount of the hydrogenated active metal becomes too small, and thus there is a possibility that the CO conversion rate is decreased, and if the supported amount exceeds the aforementioned upper limit, the hydrogenated active metal cannot be uniformly and highly dispersed, and there is a possibility that the CO conversion rate and selectivity for the C2 oxygenate, as well as the space time yield of the C2 oxygenate are decreased.

When an element belonging to group 7 of the periodic table is used as the hydrogenated active metal, a supported amount of the hydrogenated active metal is preferably 0.001 to 30 parts by mass, and more preferably 0.25 to 10 parts by mass provided that the amount of the porous carrier is 100 parts by mass. If the supported amount is less than the aforementioned lower limit, the supported amount of the hydrogenated active metal becomes too small, and thus there is a possibility that the CO conversion rate is decreased, and if the supported amount exceeds the aforementioned upper limit, the hydrogenated active metal cannot be uniformly and highly dispersed, and there is a possibility that the CO conversion rate and selectivity for the C2 oxygenate, as well as the space time yield of the C2 oxygenate are decreased.

When an element belonging to groups 8 to 10 of the periodic table is used as the hydrogenated active metal, a supported amount of the hydrogenated active metal is preferably 0.1 to 30 parts by mass, and more preferably 1 to 10 parts by mass provided that the amount of the porous carrier is 100 parts by mass. If the supported amount is less than the aforementioned lower limit, the supported amount of the hydrogenated active metal becomes too small, and thus there is a possibility that the CO conversion rate is decreased, and if the supported amount exceeds the aforementioned upper limit, the hydrogenated active metal cannot be uniformly and highly dispersed, and there is a possibility that the CO conversion rate and selectivity for the C2 oxygenate, as well as the space time yield of the C2 oxygenate are decreased.

When two or more types of hydrogenated active metals are used in combination, a supported amount of the hydrogenated active metal is determined with due consideration of the composition of the hydrogenated active metal, the type of the porous carrier and the like. For example, when the porous carrier is made from silica, the supported amount is preferably 0.05 to 30 parts by mass, and more preferably 1 to 10 parts by mass provided that the amount of the porous carrier is 100 parts by mass. If the supported amount is less than the aforementioned lower limit, there is a possibility that the CO conversion rate is decreased, and if the supported amount exceeds the aforementioned upper limit, the hydrogenated active metal cannot be uniformly and highly dispersed, and there is a possibility that the CO conversion rate and selectivity for the C2 oxygenate, as well as the space time yield of the C2 oxygenate are decreased.

In the catalyst, the supported status of the hydrogenated active metal is not particularly limited, and for example, the hydrogenated active metal may be supported on the porous carrier as the form of powder metal, or as the form of metal element. Of these, the hydrogenated active metal is supported on the porous carrier preferably as the form of metal element. If the hydrogenated active metal is supported on the porous carrier as the form of metal element, a contacting area with the mixed gas becomes large to further increase the CO conversion rate and selectivity for ethanol in the C2 oxygenate.

Not only the hydrogenated active metal, but also an auxiliary active metal may be supported in the catalyst.

Examples of the auxiliary active metal include one or more substances selected from titanium, vanadium, chromium, boron, magnesium, lanthanoid, and an element belonging to group 13 of the periodic table. Of these, for example, titanium, magnesium, and vanadium are preferable. From the viewpoint of increasing the space time yield of the C2 oxygenate, titanium is preferable. By supporting these auxiliary active metals in the catalyst, the CO conversion rate and selectivity for ethanol in the C2 oxygenate, as well as the space time yield of the C2 oxygenate can further be increased.

A supported amount of the auxiliary active metal in the catalyst is determined with due consideration of the type of the auxiliary active metal and the type of the hydrogenated active metal. For example, the supported amount is preferably 0.01 to 20 parts by mass, and more preferably 1 to 10 parts by mass provided that the amount of the porous carrier is 100 parts by mass. If the supported amount is less than the aforementioned lower limit, the supported amount of the auxiliary active metal becomes too small, and further improvement of the CO conversion rate and selectivity for the C2 oxygenate, for example, selectivity for ethanol become difficult, and further improvement of the space time yield of the C2 oxygenate, for example, the space time yield of ethanol also become difficult. If the supported amount exceeds the aforementioned upper limit, the surface of the porous carrier is covered with excess of the auxiliary active metal, and improvement of the CO conversion rate and selectivity for the C2 oxygenate, for example, selectivity for ethanol become difficult, and further improvement of the space time yield of the C2 oxygenate, for example, the space time yield of ethanol also become difficult.

In the catalyst, the supported status of the auxiliary active metal is not particularly limited, and for example, the auxiliary active metal may be supported on the porous carrier as the form of powder metal, or as the form of metal element. Of these, the auxiliary active metal is supported on the porous carrier preferably as the form of metal element. If the auxiliary active metal is supported on the porous carrier as the form of metal element, a contacting area with the mixed gas becomes large to further increase the CO conversion rate; selectivity for the C2 oxygenate, for example, selectivity for ethanol; and the space time yield of the C2 oxygenate, for example, the space time yield of ethanol.

A supported amount of the catalyst metal is determined with due consideration of the type and composition of the catalyst metal, the material of the porous carrier and the like. For example, the supported amount is preferably 0.05 to 30 parts by mass, and more preferably 1 to 10 parts by mass provided that the amount of the porous carrier is 100 parts by mass. If the supported amount is less than the aforementioned lower limit, the supported amount of the catalyst metal becomes too small, and improvement of the CO conversion rate; selectivity for ethanol; and the space time yield of the C2 oxygenate, for example, the space time yield of ethanol become difficult, and if the supported amount exceeds the aforementioned upper limit, an amount of the auxiliary active metal becomes too large to uniformly and highly disperse the hydrogenated active metal, and further improvement of the CO conversion rate; selectivity for the C2 oxygenate, for example, selectivity for ethanol; and the space time yield of the C2 oxygenate, for example, the space time yield of ethanol become difficult.

For example, the catalyst preferably contains rhodium, manganese and an alkali metal, and more preferably contains rhodium, manganese, an alkali metal and an auxiliary active metal. By using such a catalyst, the C2 oxygenate, for example ethanol can be synthesized more efficiently, and further, catalytic activity can be maintained for an extended time period.

Among the catalysts containing rhodium, manganese and alkali metals, a catalyst containing rhodium, manganese and lithium is preferable.

Among the catalysts containing rhodium, manganese, alkali metals and auxiliary active metals, a catalyst containing rhodium, manganese, lithium and magnesium, or a catalyst containing rhodium, manganese, lithium and titanium is preferable.

A composition of the catalyst containing rhodium, manganese, an alkali metal and an auxiliary active metal, preferably the catalyst containing rhodium, manganese, lithium and magnesium, or the catalyst containing rhodium, manganese, lithium and titanium is preferably represented by the formula (I) shown below:

$$aA \cdot bB \cdot cC \cdot dD \quad (I)$$

wherein A represents rhodium, B represents manganese, C represents an alkali metal such as lithium, D represents an auxiliary active metal such as magnesium and titanium, and each of a, b, c and d represents a molar fraction, wherein $a+b+c+d=1$.

In the formula (I), the value of a is preferably 0.053 to 0.98. If a is less than the aforementioned lower limit, then the amount of rhodium is too small, and there is a possibility that the efficiency of the C2 oxygenate synthesis is not enhanced sufficiently, whereas if a exceeds the aforementioned upper limit, then the amounts of other metals become too small, and there is a possibility that the efficiency of the C2 oxygenate synthesis is not enhanced sufficiently.

In the formula (I), the value of b is preferably 0.0006 to 0.67. If b is less than the aforementioned lower limit, then the amount of manganese is too small, and there is a possibility that the efficiency of the C2 oxygenate synthesis is not enhanced sufficiently, whereas if b exceeds the aforementioned upper limit, then the amounts of other metals become too small, and there is a possibility that the efficiency of the C2 oxygenate synthesis is not enhanced sufficiently.

In the formula (I), the value of c is preferably 0.00056 to 0.51. If c is less than the aforementioned lower limit, then the amount of alkali metal is too small, and there is a possibility that the efficiency of the C2 oxygenate synthesis is not enhanced sufficiently, whereas if c exceeds the aforementioned upper limit, then the amounts of other metals become too small, and there is a possibility that the efficiency of the C2 oxygenate synthesis is not enhanced sufficiently.

In the formula (I), the value of d is preferably 0.0026 to 0.94. If d is less than the aforementioned lower limit, then the amount of auxiliary active metal is too small, and there is a possibility that the efficiency of the C2 oxygenate synthesis is not enhanced sufficiently, whereas if d exceeds the aforementioned upper limit, then the amounts of other metals become too small, and there is a possibility that the efficiency of the C2 oxygenate synthesis is not enhanced sufficiently.

The catalyst of the present invention is produced in accordance with conventionally known methods for manufacturing supported catalysts. Examples of the method for manufacturing the catalyst include impregnation methods and ion exchange methods, and among these, an impregnation method is preferable. By using an impregnation method, the catalyst metal is dispersed more uniformly in the obtained catalyst, and therefore the contact efficiency with the mixed gas is further improved to further increase the CO conversion rate and selectivity for the C2 oxygenate, for example, selectivity for ethanol, and in addition, the space time yield of the C2 oxygenate, for example, the space time yield of ethanol.

Examples of the raw material compounds for the catalyst metal used in preparing the catalyst include the types of compounds typically used in preparing metal catalysts, including inorganic salts such as oxides, chlorides, sulfides, nitrates and carbonates; organic salts or chelate compounds such as oxalate salts, acetylacetonate salts, dimethylglyoxime salts and ethylenediamine acetate salts; carbonyl compounds, cyclopentadienyl compounds, amine complexes, alkoxide compounds and alkyl compounds, which are used as compounds of the catalyst metal, and among these, chlorides or sulfides are preferable.

The impregnation method is described below. First, the raw material compounds for the hydrogenated active metal, and if desired, for the auxiliary active metal are dissolved in a solvent such as water, methanol, ethanol, tetrahydrofuran, dioxane, hexane, benzene or toluene, and the porous carrier is then dipped in the thus obtained solution (impregnating solution) to adhere the impregnating solution to the porous carrier. The impregnating solution is allowed to penetrate thoroughly into the pores of the porous carrier, and the solvent is then evaporated to obtain the catalyst. In the impregnation method, a mass ratio of each of the catalyst metals contained in the impregnating solution refers to the mass ratio of each of the catalyst metals supported in the catalyst. Therefore, by employing the impregnation method for manufacturing the catalyst, the mass ratio of each of the catalyst metals contained in the catalyst can easily be controlled.

Examples of methods of impregnating the porous carrier with an impregnating solution include a method in which the porous carrier is impregnated with a solution in which all of the raw material compounds have been dissolved (simultaneous method), and a method in which each raw material compound is dissolved individually to prepare a series of solutions, and the porous carrier is then impregnated sequentially with each solution (sequential method).

Examples of the sequential method include a method in which the porous carrier is impregnated with a solution (primary impregnating solution) containing the auxiliary active metal (primary impregnation step), the porous carrier is then dried to obtain a primary support body on which the auxiliary active metal has been supported (primary support step), the primary support body is subsequently impregnated with a solution (secondary impregnating solution) containing the hydrogenated active metal (secondary impregnation step), and the support body is then dried (secondary support step). In this manner, by first supporting the auxiliary active metal on the porous carrier, and subsequently supporting the hydrogenated active metal on the porous carrier, a catalyst is obtained in which the catalyst metal is more highly dispersed to further increase the CO conversion rate and selectivity for the C2 oxygenate, for example, selectivity for ethanol, and in addition, the space time yield of the C2 oxygenate, for example, the space time yield of ethanol.

The primary support step uses a method in which, for example, the porous carrier impregnated with the primary impregnating solution is dried (primary drying operation), and the porous carrier is then heated and baked at an arbitrary temperature (primary baking step).

There are no particular limitations on the drying method used in the primary drying operation, and examples include a method in which the porous carrier impregnated with the primary impregnating solution is heated at an arbitrary temperature. The heating temperature used in the primary drying operation may be any temperature capable of evaporating the solvent of the primary impregnating solution, and when the solvent is water, the heating temperature is typically within a range from 80 to 120° C. The heating temperature in the primary baking operation is, for example, within a range from 300 to 600° C. By performing the primary baking operation, those components contained within the raw material compounds for the auxiliary active metal that do not contribute to the catalytic reaction can be satisfactorily volatilized, thereby further enhancing the catalytic activity.

The secondary support step uses a method in which, for example, the primary support body impregnated with the secondary impregnating solution is dried (secondary drying operation), and the support body is then heated and baked at an arbitrary temperature (secondary baking step).

There are no particular limitations on the drying method used in the secondary drying operation, and examples include a method in which the primary support body impregnated with the secondary impregnating solution is heated at an arbitrary temperature. The heating temperature used in the secondary drying operation may be any temperature capable of evaporating the solvent of the secondary impregnating solution, and when the solvent is water, the heating temperature is typically within a range from 80 to 120° C. The heating temperature in the secondary baking operation is, for example, within a range from 300 to 600° C. By performing the secondary baking operation, those components contained within the raw material compounds for the hydrogenated active metal that do not contribute to the catalytic reaction can be satisfactorily volatilized, thereby further enhancing the catalytic activity.

The catalyst prepared using the method described above is usually subjected to a reduction treatment to activate the catalyst, and is then used in C2 oxygenate synthesis. For the reduction treatment, a method in which the catalyst is brought into contact with a gas containing hydrogen is simple and preferable. In this case, the treatment temperature may be any temperature at which the hydrogenated active metal is reduced, for example, when the hydrogenated active metal is rhodium, the temperature is at least as large as 100° C., and is preferably within a range from 200 to 600° C. In addition, for the purpose of achieving satisfactory dispersion of the hydrogenated active metal, the hydrogen reduction may be performed while the temperature is increased from a low temperature in a gradual or stepwise manner. Further, the catalyst may also be subjected to a reduction treatment in the presence of carbon monoxide and water, or in the presence of a reducing agent such as hydrazine, a boron hydride compound, or an aluminum hydride compound.

The heating time during the reduction treatment is, for example, preferably from 1 to 10 hours, and more preferably from 2 to 5 hours. If the time is less than the aforementioned lower limit, then there is a possibility that the reduction of the catalyst metal is inadequate, and therefore the CO conversion rate and selectivity for the C2 oxygenate, for example, selectivity for ethanol, and in addition, the space time yield of the C2 oxygenate, for example, the space time yield of ethanol are decreased. If the time exceeds the aforementioned upper limit, then there is a possibility that the catalyst metal aggregates, and therefore the CO conversion rate and selectivity for the C2 oxygenate, for example, selectivity for ethanol, and in addition, the space time yield of the C2 oxygenate, for example, the space time yield of ethanol are decreased; and the energy required for the reduction treatment becomes excessive, which is economically disadvantageous.

(Device for Manufacturing C2 Oxygenate)

A device for manufacturing the C2 oxygenate according to the present invention (hereafter also referred to as simply "the manufacturing device") includes a reaction tube packed with the catalyst of the present invention, a supply unit for supplying the mixed gas into the reaction tube, and a discharge unit for discharging the product from the reaction tube.

Figure 1:
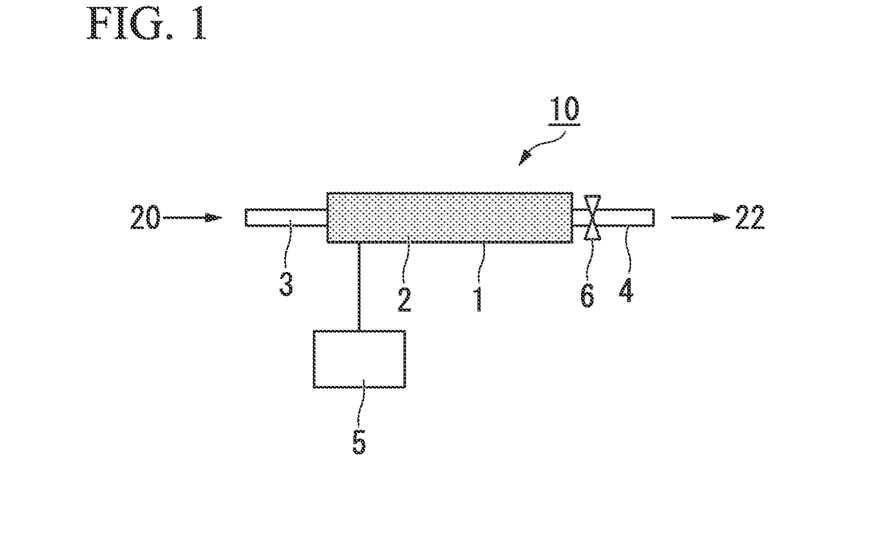
FIG. 1 is a schematic view of a device for manufacturing the C2 oxygenate according to an embodiment of the present invention.

One example of the manufacturing device of the present invention is described using FIG. 1. FIG. 1 is a schematic view illustrating a manufacturing device 10 according to an embodiment of the present invention. The manufacturing device 10 includes a reaction tube 1 which is packed with the catalyst to form a reaction bed 2, a supply tube 3 which is connected to the reaction tube 1, a discharge tube 4 which is connected to the reaction tube 1, a temperature control unit 5 which is connected to the reaction tube 1, and a pressure control unit 6 which is provided in the discharge tube 4.

The reaction tube 1 is preferably formed from a material that is inert relative to the raw material gas and the synthesized C2 oxygenate, and preferably has a shape that is resistant to heating of approximately 100 to 500° C. or pressure of approximately 10 MPa.

An example of the reaction tube 1 is a substantially circular cylindrical member formed from stainless steel.

The supply tube 3 is a supply unit for supplying the mixed gas into the reaction tube 1, and for example, is a pipe formed from stainless steel or the like.

The discharge tube 4 is a discharge unit for discharging the synthesized gas (product) containing the C2 oxygenate synthesized in the reaction bed 2, and for example, is a pipe formed from stainless steel or the like.

The temperature control unit 5 may be any device capable of adjusting the reaction bed 2 inside the reaction tube 1 to an arbitrary temperature, and examples include an electric furnace or the like.

The pressure control unit 6 may be any device capable of adjusting the pressure inside the reaction tube 1 to an arbitrary pressure, and for example, a conventional pressure valve or the like may be used.

Further, the manufacturing device 10 may also include other conventional equipment such as a mass flow or a gas flow rate control unit for adjusting the flow rate of the gas.

(Method for Manufacturing C2 Oxygenate)

A method for manufacturing the C2 oxygenate according to the present invention is a method for bringing the mixed gas into contact with the catalyst. One example of the method for manufacturing the C2 oxygenate according to the present invention is described below using the manufacturing device illustrated in FIG. 1.

First, the inside of the reaction tube 1 is set to an arbitrary temperature and an arbitrary pressure, and a mixed gas 20 is then introduced from the supply tube 3 into the reaction tube 1.

There are no particular limitations on the mixed gas 20, provided it contains hydrogen and carbon monoxide, and for example, a mixed gas prepared from natural gas or coal may be used, or a biomass gas obtained by gasifying a biomass may be used. Biomass gases can be obtained by conventionally known methods, for example by heating a pulverized biomass in the presence of steam (for example, at a temperature of 800 to 1,000° C.).

In those cases where a biomass gas is used as the mixed gas 20, the mixed gas 20 may be subjected to a gas purification treatment, for the purpose of removing impurities such as the tar fraction, sulfur fraction, nitrogen fraction, chlorine fraction and moisture fraction, prior to being supplied to the reaction tube 1. Examples of methods that may be employed as the gas purification treatment include any of the methods known within the technical field, including wet methods and dry methods. Examples of the wet methods include the sodium hydroxide method, ammonia absorption method, lime-gypsum method and magnesium hydroxide method, whereas examples of the dry methods include activated carbon adsorption methods such as the pressure swing adsorption (PSA) method, and an electron beam method.

The mixed gas 20 is preferably a gas containing hydrogen and carbon monoxide as the main components, namely a gas in which the total amount of hydrogen and carbon monoxide within the mixed gas 20 is preferably at least 50% by volume, more preferably at least 80% by volume, still more preferably 90% by volume or more, and may be 100% by volume. The larger the hydrogen and carbon monoxide content, the greater the amount of C2 oxygenate, or the greater the amount of ethanol produced.

In the mixed gas 20, the volumetric ratio represented by hydrogen/carbon monoxide (hereafter also referred to as the H$_2$/CO ratio) is preferably within a range from 1/5 to 5/1, more preferably from 1/2 to 3/1, and still more preferably from 1/1 to 2.5/1. When the ratio satisfies this range, the CO conversion rate; selectivity for the C2 oxygenate, preferably selectivity for ethanol; and the space time yield of the C2 oxygenate, preferably the space time yield of ethanol can further be increased.

Besides the hydrogen and carbon monoxide, the mixed gas 20 may also contain methane, ethane, ethylene, nitrogen, carbon dioxide, water and the like.

The temperature when the mixed gas 20 and the catalyst are brought into contact (the reaction temperature), namely the temperature inside the reaction tube 1, is preferably within a range from 150 to 450° C., more preferably from 200 to 400° C., and still more preferably from 250 to 350° C. When the temperature is at least as large as the aforementioned lower limit, the rate of the catalytic reaction can be increased satisfactorily, and the C2 oxygenate, preferably ethanol can be manufactured more efficiently. When the temperature is not greater than the upper limit, the C2 oxygenate synthesis reaction, preferably ethanol synthesis reaction becomes the main reaction, and selectivity for the C2 oxygenate, preferably selectivity for ethanol becomes increased, and thereby the C2 oxygenate, preferably ethanol can be manufactured more efficiently.

The pressure when the mixed gas 20 and the catalyst are brought into contact (the reaction pressure), namely the pressure inside the reaction tube 1, is preferably within a range from 0.5 to 10 MPa, more preferably from 1 to 7.5 MPa, and still more preferably from 2 to 5 MPa. When the pressure is at least as large as the aforementioned lower limit, the rate of the catalytic reaction can be increased satisfactorily, and the C2 oxygenate, preferably ethanol can be manufactured more efficiently. When the pressure is not greater than the upper limit, the C2 oxygenate synthesis reaction, preferably ethanol synthesis reaction becomes the main reaction, and selectivity for the C2 oxygenate, preferably selectivity for ethanol becomes increased, and thereby the C2 oxygenate, preferably ethanol can be manufactured more efficiently.

The introduced mixed gas 20 flows through the reaction tube while making contact with the catalyst in the reaction bed 2, and a portion of the mixed gas is converted to the C2 oxygenate.

While flowing through the reaction bed 2, the mixed gas 20 generates C2 oxygenate compounds, for example by the catalytic reactions represented by the formulae (1) to (5) shown below. In the present invention, the catalytic reaction represented by the formula (5) occurs mainly, and also, acetic acid or acetaldehyde generated by the catalytic reaction represented by the formula (1) or (2) becomes ethanol by the catalytic reaction represented by the formula (3) or (4).

$$2H_2 + 2CO \rightarrow CH_3COOH \tag{1}$$

$$3H_2 + 2CO \rightarrow CH_3CHO + H_2O \tag{2}$$

$$2H_2 + CH_3COOH \rightarrow CH_3CH_2OH + H_2O \tag{3}$$

$$H_2 + CH_3CHO \rightarrow CH_3CH_2OH \tag{4}$$

$$4H_2 + 2CO \rightarrow CH_3CH_2OH + H_2O \tag{5}$$

A synthesis gas 22 containing these C2 oxygenates is discharged from the discharge tube 4. There are no particular limitations on the synthesis gas 22 provided it contains the C2 oxygenate, preferably ethanol, and it may also contains products other than ethanol (for example, C2 oxygenates except for ethanol, such as acetic acid and acetaldehyde; oxygenates such as esters including ethyl acetate, methyl acetate and methyl formate; and hydrocarbons such as methane).

In the synthesis gas 22, selectivity for the C2 oxygenate is preferably at least as large as 60 mol %, and more preferably at least as large as 80 mol %. If selectivity of the C2 oxygenate is at least as large as the aforementioned lower limit, greater amount of the C2 oxygenate can be produced.

Although the amount of the C2 oxygenate in oxygenates contained in the synthesis gas 22 is not particularly limited, it is preferably at least as large as 60 mol %, and more preferably at least as large as 80 mol %. If the amount is at least as large as the aforementioned lower limit, greater amount of the C2 oxygenate can be produced.

Although the amount of ethanol in the C2 oxygenate contained in the synthesis gas 22 is not particularly limited, it is preferably at least as large as 55 mol %, and more preferably at least as large as 70 mol %.

If the amount is at least as large as the aforementioned lower limit, steps for removing products other than ethanol, and for converting products other than ethanol into ethanol can be simplified.

In the method for manufacturing the C2 oxygenate according to the present invention, a space time yield of the C2 oxygenate is preferably 650 (g/L-catalyst/h) to 180 (g/L-catalyst/h). If the space time yield is within the aforementioned range, the C2 oxygenate can be synthesized with high efficiency.

In addition, in the method for manufacturing the C2 oxygenate according to the present invention, selectivity for ethanol in the C2 oxygenate is preferably 96 mol % to 35 mol %. If selectivity for ethanol is at least as large as the lower limit, separation and purification are advantageously facilitated.

The supply rate of the mixed gas 20 is, for example, the space velocity of the mixed gas in the reaction bed 2 (the value obtained by dividing the gas supply volume per unit of time by the amount of the catalyst (converted to volume)), calculated as a standard state value, is preferably 10 to 100,000 L/L-catalyst/h, more preferably 1,000 to 50,000 L/L-catalyst/ h, and still more preferably 3,000 to 20,000 L/L-catalyst/h. The space velocity is adjusted as appropriate, with due consideration of the reaction pressure and reaction temperature and the composition of the mixed gas that represents the raw material.

If necessary, the synthesis gas 22 discharged from the discharge tube 4 may be processed in a gas-liquid separator or the like to separate the unreacted mixed gas 20 and the C2 oxygenate.

In the present embodiment, the mixed gas is brought into contact with the fixed bed of the reaction bed 2, but the catalyst may also be formed in a configuration other than a fixed bed, such as a fluidized bed or a moving bed, and the mixed gas then brought into contact with this bed.

In the present invention, the obtained C2 oxygenate may, if necessary, be separated into the required components using distillation or the like.

Further, in the present invention, a step of hydrogenating products other than ethanol and converting these products to ethanol (an ethanolization step) may also be provided. An example of the ethanolization step is a method in which the C2 oxygenate including acetaldehyde and acetic acid and the like are brought into contact with a hydrogenation catalyst to effect a conversion to ethanol.

The types of catalysts known in this technical field can be used as the hydrogenation catalyst, and examples include copper, copper-zinc, copper-chromium, copper-zinc-chromium, iron, rhodium-iron, rhodium-molybdenum, palladium, palladium-iron, palladium-molybdenum, iridium-iron, rhodium-iridium-iron, iridium-molybdenum, rhenium-zinc, platinum, nickel, cobalt, ruthenium, rhodium oxide, palladium oxide, platinum oxide and ruthenium oxide. These hydrogenation catalysts may be supported catalysts in which the catalyst is supported on the same type of porous carrier as that used in the catalyst of the present invention, and supported copper catalysts in which copper, copper-zinc, copper-chromium or copper-zinc-chromium are supported on a silica-based carrier are ideal. Examples of the method for manufacturing the supported hydrogenation catalyst include the same simultaneous and sequential methods as those described for the catalyst of the present invention.

As described above, by using the catalyst of the present invention, selectivity for ethanol in the C2 oxygenate can be increased, or the space time yield of the C2 oxygenate can be increased, and thereby the C2 oxygenate, preferably ethanol can be synthesized efficiently. That is, by increasing selectivity for ethanol in the C2 oxygenate, separation and purification can be facilitated. In addition, by increasing the space time yield of the C2 oxygenate, an amount of the C2 oxygenate produced can be increased.

Although a principle of the present invention to allow efficient syntheses of ethanol is unclear, it can be assumed as described below.

When the mixed gas is brought into contact with the catalyst, if an average pore diameter of the porous carrier is 0.1 to 8 nm, the mixed gas leaches into, and out from the pores slower, which means the mixed gas is retained in the pores longer to contact with the catalyst metal supported in the pores longer. Since the contacting time between the mixed gas and the catalyst metal described above is suitable for the catalytic reactions represented by the formulae (3) to (5), in particular, suitable for the catalytic reaction represented by the formula (5), selectivity for ethanol is increased to efficiently synthesize ethanol.

However, if an average pore diameter of the porous carrier is less than 2 nm, the mixed gas leaches into, and out from the pores too slow, which means that although the mixed gas leached into the pores contacts with the catalyst metal sufficiently longer to be converted into the C2 oxygenate, the mixed gas leaches into, and out from the pores less frequently to increase the CO conversion rate. Thus, when an average pore diameter is less than 2 nm, the space time yield of the C2 oxygenate cannot be increased.

If an average pore diameter of the porous carrier exceeds 20 nm, the mixed gas leaches into, and out from the pores too fast, which means that although the mixed gas leaches into, and out from the pores more frequently, the contacting time between the mixed gas leached into the pores and the catalyst metal becomes insufficient to convert the mixed gas into the C2 oxygenate. Thus, when an average pore diameter exceeds 20 nm, selectivity of the C2 oxygenate is decreased, and the space time yield of the C2 oxygenate cannot be increased.

Accordingly, if an average pore diameter of the porous carrier is 2 to 20 nm, the mixed gas can be retained in the pores during the time period suitable to increase the space time yield of the C2 oxygenate.

EXAMPLES

The present invention is described below using a series of examples, but the present invention is in no way limited by these examples.

Example 1-1

First, 0.58 mL of an aqueous solution containing 0.049 g of an ammonium titanium lactate salt $(Ti(OH)_2[OCH(CH_3)COO^-]_2(NH_4^+)_2)$ (the primary impregnating solution) was added dropwise to 2.0 g of a porous carrier (material: silica, particle size: 1.18 to 2.36 mm, average pore diameter: 1.9 nm, total pore volume: 0.29 mL/g, specific surface area: 620 m$^2$/g) to impregnate the porous carrier (the primary impregnation step). The resulting mixture was dried at 110° C. for 3 hours (the primary drying operation), and then baked at 400° C. for 4.5 hours to obtain a primary support body (the primary baking operation, the above represents the primary support step). Subsequently, 0.6 mL of an aqueous solution containing 0.154 g of rhodium chloride trihydrate ($RhCl_3.3H_2O$), 0.087 g of manganese chloride dihydrate ($MnCl_2.2H_2O$), and 0.01 g of lithium chloride monohydrate ($LiCl.H_2O$) (the secondary impregnating solution) was added dropwise to the primary support body to impregnate the primary support body (the secondary impregnation step), and the resulting mixture was dried at 110° C. for 3 hours (the secondary drying operation) and then baked at 400° C. for 4.5 hours to obtain a catalyst (the secondary baking operation, the above represents the secondary support step). The molar ratio of hydrogenated active metals in the total of the primary impregnating solution and the secondary impregnating solution was rhodium:manganese=1:0.75, rhodium:lithium=1:0.275, and manganese:lithium=1:0.667.

Example 1-2

With the exception of not conducting the primary impregnation step and the primary support step, a catalyst was obtained in the same manner as Example 1-1. The molar ratio of hydrogenated active metals in the secondary impregnating solution was rhodium:manganese=1:0.75, rhodium:lithium=1:0.275, and manganese:lithium=1:0.667.

Example 1-3

With the exception of that 1.22 mL of an aqueous solution containing 0.049 g of an ammonium titanium lactate salt (the primary impregnating solution) was added dropwise to 2.0 g of a porous carrier (material: silica, particle size: 1.18 to 2.36 mm, average pore diameter: 5.7 nm, total pore volume: 0.61 mL/g, specific surface area: 430 m²/g) to impregnate the porous carrier in the primary impregnation step, a catalyst was obtained in the same manner as Example 1-1. The molar ratio of hydrogenated active metals in the total of the primary impregnating solution and the secondary impregnating solution was rhodium:manganese=1:0.75, rhodium:lithium=1:0.275, and manganese:lithium=1:0.667.

Example 1-4

With the exception of not conducting the primary impregnation step and the primary support step, a catalyst was obtained in the same manner as Example 1-3. The molar ratio of hydrogenated active metals in the secondary impregnating solution was rhodium:manganese=1:0.75, rhodium:lithium=1:0.275, and manganese:lithium=1:0.667.

Example 1-5

First, 2.16 mL of an aqueous solution containing 0.123 g of an ammonium titanium lactate salt (the primary impregnating solution) was added dropwise to 2.0 g of a porous carrier (material: silica, particle size: 0.7 to 2.0 mm, average pore diameter: 13.7 nm, total pore volume: 1.08 mL/g, specific surface area: 315 m²/g) to impregnate the porous carrier (the primary impregnation step). The resulting mixture was dried at 110° C. for 3 hours (the primary drying operation), and then baked at 400° C. for 4.5 hours to obtain a primary support body (the primary baking operation, the above represents the primary support step). Subsequently, 2.16 mL of an aqueous solution containing 0.154 g of rhodium chloride trihydrate, 0.032 g of manganese chloride dihydrate, and 0.005 g of lithium chloride monohydrate (the secondary impregnating solution) was added dropwise to the primary support body to impregnate the primary support body (the secondary impregnation step), and the resulting mixture was dried at 110° C. for 3 hours (the secondary drying operation) and then baked at 400° C. for 4.5 hours to obtain a catalyst (the secondary baking operation, the above represents the secondary support step). The molar ratio of hydrogenated active metals in the total of the primary impregnating solution and the secondary impregnating solution was rhodium:manganese=1:0.275, rhodium:lithium=1:0.138, and manganese:lithium=1:0.5.

Example 1-6

With the exception of not conducting the primary impregnation step and the primary support step, a catalyst was obtained in the same manner as Example 1-5. The molar ratio of hydrogenated active metals in the secondary impregnating solution was rhodium:manganese=1:0.75, rhodium:lithium=1:0.275, and manganese:lithium=1:0.667.

Example 1-7

With the exception of that 0.58 mL of an aqueous solution containing 0.123 g of an ammonium titanium lactate salt (the primary impregnating solution) was added dropwise to 2.0 g of a porous carrier (material: silica, particle size: 1.18 to 2.36 mm, average pore diameter: 1.9 nm, total pore volume: 0.29 mL/g, specific surface area: 620 m²/g) to impregnate the porous carrier in the primary impregnation step, and 2.16 mL of an aqueous solution containing 0.154 g of rhodium chloride trihydrate, 0.032 g of manganese chloride dihydrate, and 0.005 g of lithium chloride monohydrate (the secondary impregnating solution) was added dropwise to the primary support body to impregnate the primary support body in the secondary impregnation step, a catalyst was obtained in the same manner as Example 1-1. The molar ratio of hydrogenated active metals in the secondary impregnating solution was rhodium:manganese=1:0.75, rhodium:lithium=1:0.275, and manganese:lithium=1:0.667.

Comparative Example 1-1

With the exception of that 1.96 mL of an aqueous solution containing 0.123 g of an ammonium titanium lactate salt (the primary impregnating solution) was added dropwise to 2.0 g of a porous carrier (material: silica, particle size: 1.18 to 2.36 mm, average pore diameter: 31.1 nm, total pore volume: 0.98 mL/g, specific surface area: 107 m²/g) to impregnate the porous carrier in the primary impregnation step, a catalyst was obtained in the same manner as Example 1-1.

The molar ratio of hydrogenated active metals in the total of the primary impregnating solution and the secondary impregnating solution was rhodium:manganese=1:0.75, rhodium:lithium=1:0.275, and manganese:lithium=1:0.667.

<Evaluation Method>

A 0.5 g of the catalyst from each of Examples 1-1 to 1-7, and Comparative Example 1-1 was packed in a circular cylindrical reaction tube formed from stainless steel having a diameter of 0.5 inches (1.27 cm) and a length of 10 inches (25.4 cm), thus forming a reaction bed. The reaction bed was heated at 320° C. for 2.5 hours while hydrogen-nitrogen gas (H2/N2=½) was passed through the reaction bed at normal pressure at a rate of 30 mL/minutes, thereby subjecting the catalyst to a reduction treatment.

Subsequently, a temperature of the reaction bed was adjusted to 250° C., and then the reaction temperature shown in Table 1 was applied to the reaction bed. After that, a mixed gas ($H_2$/CO ratio=2/1) was passed through the reaction bed at a space velocity of 8400 L/L-catalyst/h, or 12000L/L-catalyst/h, 2 MPa, and a synthesis gas containing the C2 oxygenate was manufactured.

The mixed gas was passed through the reaction bed for 3 hours, and the obtained synthesis gas was collected and analyzed by gas chromatography.

From the thus obtained data, the CO conversion rates (mol %), the values of selectivity for C2 oxygenates (mol %), the value of selectivity for each of the products (mol %), and the space time yields of the C2 oxygenates (g/L-catalyst/h) were calculated. These results are shown in Table 1. The space time yield of the C2 oxygenate is a value obtained when all C2 oxygenates obtained are assumed to be converted into ethanol by a well-known hydrogen reduction treatment (for example, catalytic hydrogen reduction). In the table, a proportion of ethanol in the C2 oxygenate was calculated as an amount of ethanol within a total amount of ethanol, acetaldehyde and acetic acid (that is, a total amount of the C2 oxygenate) contained in the product.

TABLE 1

|  | Example | | | | | | | Comparative Example |
|---|---|---|---|---|---|---|---|---|
|  | 1-1 | 1-2 | 1-3 | 1-4 | 1-5 | 1-6 | 1-7 | 1-1 |
| Average Pore Diameter of Porous Carrier (nm) | 1.9 | 1.9 | 5.7 | 5.7 | 13.7 | 13.7. | 1.9 | 31.1 |
| Specific Surface Area of Porous Carrier (m$^2$/g) | 620 | 620 | 430 | 430 | 315 | 315 | 620 | 107 |
| Total Pore Volume of Porous Carrier (mL/g) | 0.29 | 0.29 | 0.61 | 0.61 | 1.08 | 1.08 | 0.29 | 0.98 |
| Reaction Temperature (° C.) | 286 | 287 | 286 | 288 | 294 | 292 | 293 | 288 |
| Selectivity (mol %) Ethanol | 60.7 | 32.3 | 40.1 | 23.0 | 12.3 | 13.9 | 56.9 | 15.8 |
| Acetaldehyde | 2.4 | 9.4 | 27.7 | 35.7 | 40.2 | 49.6 | 4.0 | 37.0 |
| Acetic Acid | 0.2 | 0.0 | 0.1 | 0.0 | 1.9 | 0.0 | 0.7 | 0.0 |
| Proportion of Ethanol in C2 oxygenate (mol %) | 95.9 | 77.5 | 59.1 | 39.1 | 22.6 | 21.9 | 92.4 | 29.9 |
| CO Conversion Rate (mol %) | 11.2 | 6.7 | 34.9 | 24.6 | 31.5 | 14.5 | 11.6 | 8.9 |
| Space Time Yield of C2 Oxygenate (g/L-catalyst/h) | 185.0 | 73.1 | 618.2 | 377.0 | 445.6 | 239.9 | 186.0 | 122.5 |

As illustrated in Table 1, Examples 1-1 to 1-7 applicable to the present invention exhibited selectivity for ethanol of at least as large as 12.3 mol %, and a proportion of ethanol in the C2 oxygenate of at least as large as 22.6 mol %.

Of these, in Examples 1-1 to 1-4, and 1-7, in which average pore diameters were less than 8 nm, selectivity for ethanol was at least as large as 23.0 mol %, and proportions of ethanol in the C2 oxygenate was at least as large as 39.1 mol %. When Examples 1-1 and 1-2, or Examples 1-3 and 1-4 are compared, since the supported auxiliary active metals were employed in Examples 1-1 and 1-3, selectivity for ethanol and proportions of ethanol in the C2 oxygenate were increased in Examples 1-1 and 1-3, compared with Examples 1-2 and 1-4 respectively.

In Examples 1-5 and 1-6, in which porous carriers having average pore diameters greater than 8 nm were employed, selectivity for ethanol and proportions of ethanol in the C2 oxygenate were decreased compared to those in Examples 1-1 to 1-4; however, selectivity for the C2 oxygenates were at least as large as 50 mol %, and the space time yields of the C2 oxygenates were also at least as large as 200 (g/L-catalyst/h) in both Examples 1-5 and 1-6.

On the other hand, in Comparative Example 1-1, selectivity for ethanol was not greater than 15.8 mol %, a proportion of ethanol in the C2 oxygenate was not greater than 29.9 mol %, and a space time yield of the C2 oxygenate was 122.5 (g/L-catalyst/h). Based on these results it was evident that by applying the present invention, ethanol could be synthesized efficiently from the mixed gas.

Example 2

By using the catalyst obtained in Example 1-1, and with the exception of that the reaction temperatures shown in Table 2 were applied, synthesis gases containing the C2 oxygenates were manufactured in the same manner as Example 1-1, and the value of selectivity for each of the products (mol %) was calculated. The obtained results are shown in Table 2 and FIG. 2. In Table 2 and FIG. 2, a proportion of ethanol in the C2 oxygenate was calculated as an amount of ethanol within a total amount of ethanol, acetaldehyde and acetic acid (that is, a total amount of the C2 oxygenate) contained in the product.

TABLE 2

|  | Example 2 | | | |
|---|---|---|---|---|
| Average Pore Diameter of Porous Carrier (nm) | 1.9 | | | |
| Specific Surface Area of Porous Carrier (m$^2$/g) | 620 | 620 | 620 | 620 |
| Reaction Temperature (° C.) | 272 | 282 | 293 | 305 |
| Selectivity (mol %) Ethanol | 56.2 | 60.1 | 56.9 | 45.5 |
| Acetaldehyde | 4.2 | 5.5 | 4.0 | 2.2 |
| Acetic Acid | 0.2 | 0.2 | 0.7 | 0.2 |
| Proportion of Ethanol in C2 oxygenate (mol %) | 92.6 | 91.3 | 92.4 | 94.8 |

Figure 2:
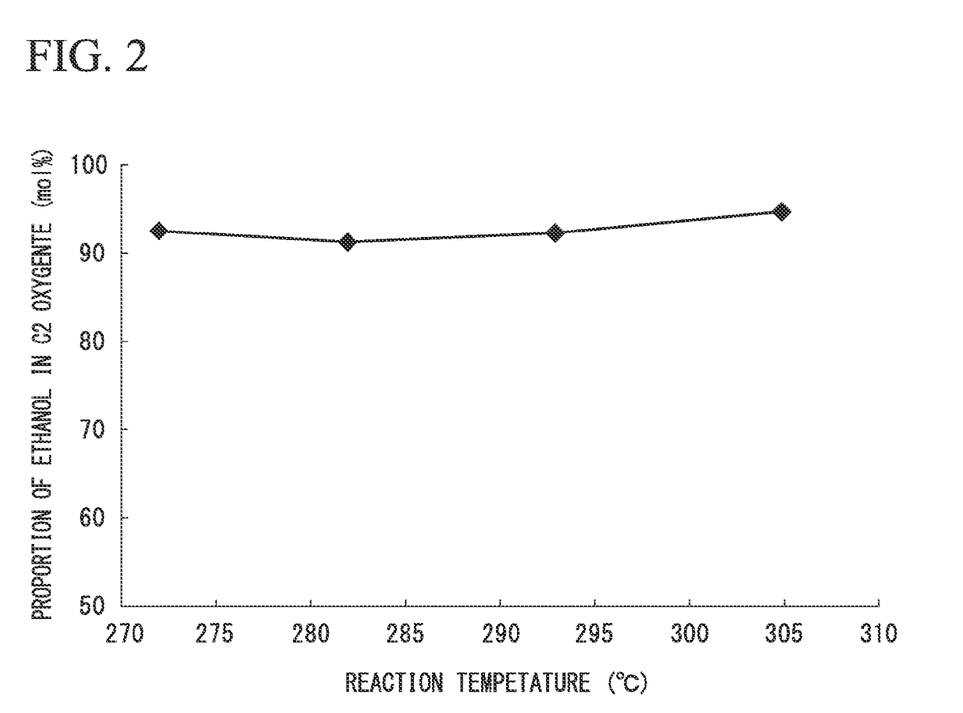
FIG. 2 is a graph showing the result of Example 2.

In the graph of FIG. 2, the horizontal axis indicates reaction temperatures, and the vertical axis indicates proportions of ethanol in the C2 oxygenate (mol %).

As shown in Table 2 and FIG. 2, the result of Example 2 indicates that the proportion of ethanol in the C2 oxygenate could be at least as large as 90 mol % when the reaction temperature was in the range of 272 to 305° C.

DESCRIPTION OF THE REFERENCE SIGNS

1: Reaction tube
2: Reaction bed
3: Supply tube
4: Discharge tube
5: Temperature control unit
6: Pressure control unit
10: Manufacturing device
20: Mixed gas
22: Synthesis gas

The invention claimed is:

1. A catalyst for C2 oxygenate synthesis from a mixed gas containing hydrogen and carbon monoxide, the catalyst comprising rhodium, manganese and lithium as hydrogenated active metals, and titanium as an auxiliary active metal, which are supported on a porous carrier, wherein the porous carrier has an average pore diameter of 0.1 to 20 nm.

2. The catalyst for C2 oxygenate synthesis according to claim 1, wherein the average pore diameter is 0.1 to 8 nm.

3. The catalyst for C2 oxygenate synthesis according to claim 1, wherein the average pore diameter is 2 to 20 nm.

4. The catalyst for C2 oxygenate synthesis according to claim 1, wherein a specific surface area of the porous carrier is 315 to 700 $m^2/g$.

5. The catalyst for C2 oxygenate synthesis according to claim 4, wherein a value represented by (total pore volume)/(specific surface area×average pore diameter) of the porous carrier is 0.2 to 0.5.

* * * * *